(12) United States Patent
Younes et al.

(10) Patent No.: US 8,693,743 B1
(45) Date of Patent: Apr. 8, 2014

(54) ANALYSIS AND DISPLAY OF MULTIPLE BIOMARKER CO-EXPRESSION IN CELLS AND TISSUES

(75) Inventors: Mamoun Younes, Houston, TX (US); David Frederick Wiley, Woodland, CA (US)

(73) Assignee: Olive Tree Media, LLC, Houston, TX (US)

( * ) Notice: Subject to any disclaimer, the term of this patent is extended or adjusted under 35 U.S.C. 154(b) by 1025 days.

(21) Appl. No.: 12/709,152

(22) Filed: Feb. 19, 2010

(51) Int. Cl.
*G06K 9/00* (2006.01)

(52) U.S. Cl.
USPC .......................................................... 382/128

(58) Field of Classification Search
None
See application file for complete search history.

(56) References Cited

U.S. PATENT DOCUMENTS

| | | | |
|---|---|---|---|
| 3,819,913 | A | 6/1974 | Carter et al. |
| 4,891,692 | A | 1/1990 | Outa |
| 5,099,521 | A | 3/1992 | Kosaka |
| 5,309,228 | A | 5/1994 | Nakamura |
| 5,353,132 | A | 10/1994 | Katsuma |
| 5,546,323 | A | 8/1996 | Bacus et al. |
| 5,748,771 | A | 5/1998 | Fujiwara |
| 5,933,524 | A | 8/1999 | Schuster et al. |
| 5,949,556 | A | 9/1999 | Tamai |
| 5,982,944 | A | 11/1999 | Vaidyanathan et al. |
| 6,064,775 | A | 5/2000 | Suzuki et al. |
| 6,118,895 | A | 9/2000 | Hirota et al. |
| 6,351,556 | B1 | 2/2002 | Loui et al. |
| 6,411,730 | B1 | 6/2002 | Bartell et al. |
| 6,532,301 | B1 | 3/2003 | Krumm et al. |
| 6,608,926 | B1 | 8/2003 | Suwa et al. |
| 6,711,287 | B1 | 3/2004 | Iwasaki |
| 6,718,056 | B1 | 4/2004 | Bothorel et al. |
| 6,775,408 | B1 | 8/2004 | Masaki |
| 6,781,595 | B2 | 8/2004 | Kobayashi et al. |
| 6,947,597 | B2 | 9/2005 | Lin et al. |
| 6,952,496 | B2 | 10/2005 | Krumm |
| 6,975,758 | B2 | 12/2005 | Nicolas |

(Continued)

FOREIGN PATENT DOCUMENTS

| | | |
|---|---|---|
| EP | 0574831 A1 | 12/1993 |
| EP | 0807297 A2 | 11/1997 |
| EP | 0759599 A2 | 12/1997 |
| EP | 1265190 A1 | 12/2002 |
| EP | 1347393 A1 | 9/2003 |
| EP | 1452995 A2 | 9/2004 |
| JP | 59114667 U | 8/1984 |
| JP | 01298485 A | 12/1989 |
| JP | 07073325 A | 3/1995 |
| JP | 08212296 A | 8/1996 |
| JP | 2001076096 A | 3/2001 |
| JP | 2001118031 A | 4/2001 |
| JP | 2002042055 A | 2/2002 |
| JP | 2002190018 A | 7/2002 |
| JP | 2003196591 A | 7/2003 |
| JP | 2003216894 A | 7/2003 |
| JP | 2005260657 A | 9/2005 |

OTHER PUBLICATIONS

Hatchet-Haas FRET and Colocalization Analyzer obtained via http://web.archive.org/web/20090508161616/http://rsbweb.nih.gov/ij/plugins/fret-analyzer/download/FRET%20and%20Colocalization%20Analyzer%20-%20User%20guide.pdf for the date May 8, 2009.*

*Primary Examiner* — Eliza Lam
(74) *Attorney, Agent, or Firm* — Osha •Liang LLP

(57) ABSTRACT

A method for analyzing a tissue specimen that includes obtaining a first digital tissue sample image and a second digital tissue sample image showing a first and a second tissue sample, respectively. The first tissue sample and the second tissue sample are stained for a first biomarker and a second biomarker, respectively. Both digital tissue sample images are analyzed to identify portions of the first tissue sample positive for the first biomarker and for the second biomarker, respectively. A co-expression analysis to create a biomarker co-expression profile. The co-expression analysis identifies at least a portion of the tissue specimen positive for both the first biomarker and the second biomarker, at least a portion of the tissue specimen positive for only the first biomarker, and at least a portion of the tissue specimen positive for only the second biomarker. The biomarker co-expression profile is displayed.

21 Claims, 11 Drawing Sheets

(56) References Cited

U.S. PATENT DOCUMENTS

| | | |
|---|---|---|
| 2003/0179926 A1 | 9/2003 | Yamazoe et al. |
| 2004/0190789 A1 | 9/2004 | Liu et al. |
| 2004/0197022 A1 | 10/2004 | Gonsalves |
| 2004/0208365 A1 | 10/2004 | Loui et al. |
| 2005/0008222 A1 | 1/2005 | Gallina |
| 2005/0013485 A1 | 1/2005 | Masaki |
| 2005/0052665 A1 | 3/2005 | Moroney |
| 2005/0088534 A1 | 4/2005 | Shen et al. |
| 2005/0100212 A1 | 5/2005 | Eguchi et al. |
| 2005/0163385 A1 | 7/2005 | Thakur |
| 2005/0238229 A1 | 10/2005 | Ishidera |
| 2011/0091377 A1* | 4/2011 | Alani et al. .................. 424/1.49 |

\* cited by examiner

ANALYSIS AND DISPLAY OF MULTIPLE BIOMARKER CO-EXPRESSION IN CELLS AND TISSUES

BACKGROUND

Targeted therapy is a mechanism for using drugs designed to target specific biomarkers to treat a disease. Because the drugs are only effective in regard to a specific corresponding biomarker, targeted therapy requires an initial determination as to whether a patient will respond to a given drug treatment based upon whether or not the specific target biomarker is present within the diseased cells. Thus, the effectiveness of a drug depends on the level of expression of the biomarker in diseased cells and tissues taken as a sample from the patient.

A biomarker is a protein, peptide, sugar, RNA, deoxyribonucleic acid (DNA), or gene within cells or tissues. The expression of the biomarker correlates to a specific biologic event and/or response to treatment with a specific agent or drug.

The following examples illustrate a scenario in which estrogen receptor (a protein) expression, Her2 gene copy number, thymidylate synthase RNA levels, and p53 protein are all biomarkers. In the first example, an expression of Estrogen receptor in breast cancer cells correlates with better response to treatment in women with breast cancer treated with the drug, Tamoxifen, which targets the Estrogen receptor. As a second example, increased copy number (i.e., an increase in the number of copies) of the Her2 gene, or an increased Her2 protein, in breast cancer cells correlates with better survival (treatment response) in women with breast cancer treated with transtuzumab (e.g., Herceptin®), which targets the Her2 receptor. As a third example, expression of thymidylate synthase (TS) protein or RNA in colon cancer cells correlates with resistance to the drug 5-fluorouracil (5-FU). As a final example, an increased expression of p53 protein in a condition known as Barrett's esophagus correlates with increased risk for cancer of the esophagus. Although the above examples discusses treatment of cancer cells, biomarkers are useful in treating many different diseases.

In order to determine whether a targeted drug will be effective, a patient tissue sample is first evaluated to determine whether the target biomarker for a given drug is present within the tissue sample. Specifically, because not all cancer cells express the biomarker, whether a biomarker is present in the cancer cells needs to be first determined prior to determining whether the drug targeting the biomarker is effective. Specifically, some cells may completely lack the biomarker or express low quantities of the biomarker that are not sufficient to produce the desired effect when the drug is given.

For example, if drug "A" targets protein "a", but biomarker analysis of the tissue shows only 40% of the cancer cells test positive for biomarker "a", then a second drug must be used to address the remaining 60% of cells. In such a scenario, it is common for several drugs to be used in combination to address the patient-specific disease profile. Determination of the patient-specific disease profile is the goal of biomarker analysis.

Several methods exist to assess a single biomarker expression level in tissues and cell lines. The existing methods are successful to determine the likelihood of successful treatment using a single drug based upon the biomarker expression ratio specific to the single drug. However, when a single drug does not sufficiently treat all diseased cell classes, a drug profile corresponding to multiple biomarkers must be obtained in order to develop an adequate treatment plan employing a combination of drugs.

For example, to determine if a patient will respond to treatment with drugs "A", "B", "C" and/or "D", a pathologist must first determine the patient-specific disease profile of the biomarker targets "a", "b", "c", and "d", respectively for each drug. Specifically, the pathologist determines the expression of, or the percentage of cells positive for each biomarker in the patient's tissue sample.

The above techniques, however, do not establish the co-expression relationship among biomarkers. To continue with the example, using current methods, the results could be reported as: 50% of the cancer cells are positive for biomarker "a", 20% of cells are positive for "b", 30% are positive for "c", and 10% positive for "d".

The results suggest that using all drugs in combination (A, B, C, and D) will kill all of the cancer cells. However, because of potential overlap between the cells having each biomarker, it is possible that not all cancer cells will be killed. For example, it is possible that all cells that are positive for "b" and "c" are also positive for "a" while cells positive for "d" do not co-express any other biomarker. In such a scenario, drugs "B" and "C" target diseased cells already addressed by drug "A", and using all four drugs will kill only 60% of the cells (50% for "a,b,c" and 10% for "d"), possibly leaving 40% of the diseased cells free to proliferate and ultimately kill the patient.

Further, most cancer drugs have toxic side effects. Therefore, it is in the patient's best interest to optimize drug therapy in regard to i) effectiveness and ii) side effects. In our example, if drug "B" or "C" has adverse side effects, the physician could withhold both drugs and achieve the same treatment outcome while improving the patient's quality of life. However, the patient may still die because the therapy did not address a significant portion of diseased cells with the chosen drug combination.

SUMMARY

In general, in one aspect, the invention relates to a method for analyzing a tissue specimen. The method includes obtaining a first digital tissue sample image showing a first tissue sample, wherein the first tissue sample is stained for a first biomarker and obtaining a second digital tissue sample image showing a second tissue sample, wherein the second tissue sample is stained for a second biomarker. The first digital tissue sample image is analyzed to identify portions of the first tissue sample positive for the first biomarker. The second digital tissue sample image is analyzed to identify portions of the second tissue sample positive for the second biomarker. A co-expression analysis of portions of the first tissue sample positive for the first biomarker and the portions of the second tissue sample positive for the second biomarker is performed to create a biomarker co-expression profile. The co-expression analysis identifies at least a portion of the tissue specimen positive for both the first biomarker and the second biomarker, at least a portion of the tissue specimen positive for only the first biomarker, and at least a portion of the tissue specimen positive for only the second biomarker. The biomarker co-expression profile is displayed.

In general, in one aspect, the invention relates to a system for analyzing a tissue specimen that includes a processor, a memory, and instructions. The instructions are stored in memory and cause the processor to obtain a first digital tissue sample image showing a first tissue sample, wherein the first tissue sample is stained for a first biomarker and obtain a second digital tissue sample image showing a second tissue sample, wherein the second tissue sample is stained for a second biomarker. The first digital tissue sample image is analyzed to identify portions of the first tissue sample positive for the first biomarker. The second digital tissue sample image is analyzed to identify portions of the second tissue sample positive for the second biomarker. A co-expression analysis of portions of the first tissue sample positive for the first biomarker and the portions of the second tissue sample positive for the second biomarker is performed to create a biomarker co-expression profile. The co-expression analysis identifies at least a portion of the tissue specimen positive for both the first biomarker and the second biomarker, at least a portion of the tissue specimen positive for only the first biomarker, and at least a portion of the tissue specimen positive for only the second biomarker. The biomarker co-expression profile is displayed.

In general, in one aspect, the invention relates to a computer readable medium comprising computer readable program code stored thereon. The computer readable program code causes the processor to obtain a first digital tissue sample image showing a first tissue sample, wherein the first tissue sample is stained for a first biomarker and obtain a second digital tissue sample image showing a second tissue sample, wherein the second tissue sample is stained for a second biomarker. The first digital tissue sample image is analyzed to identify portions of the first tissue sample positive for the first biomarker. The second digital tissue sample image is analyzed to identify portions of the second tissue sample positive for the second biomarker. A co-expression analysis of portions of the first tissue sample positive for the first biomarker and the portions of the second tissue sample positive for the second biomarker is performed to create a biomarker co-expression profile. The co-expression analysis identifies at least a portion of the tissue specimen positive for both the first biomarker and the second biomarker, at least a portion of the tissue specimen positive for only the first biomarker, and at least a portion of the tissue specimen positive for only the second biomarker. The biomarker co-expression profile is displayed.

Other aspects of the invention will be apparent from the following description and the appended claims.

DETAILED DESCRIPTION

Figure 1:
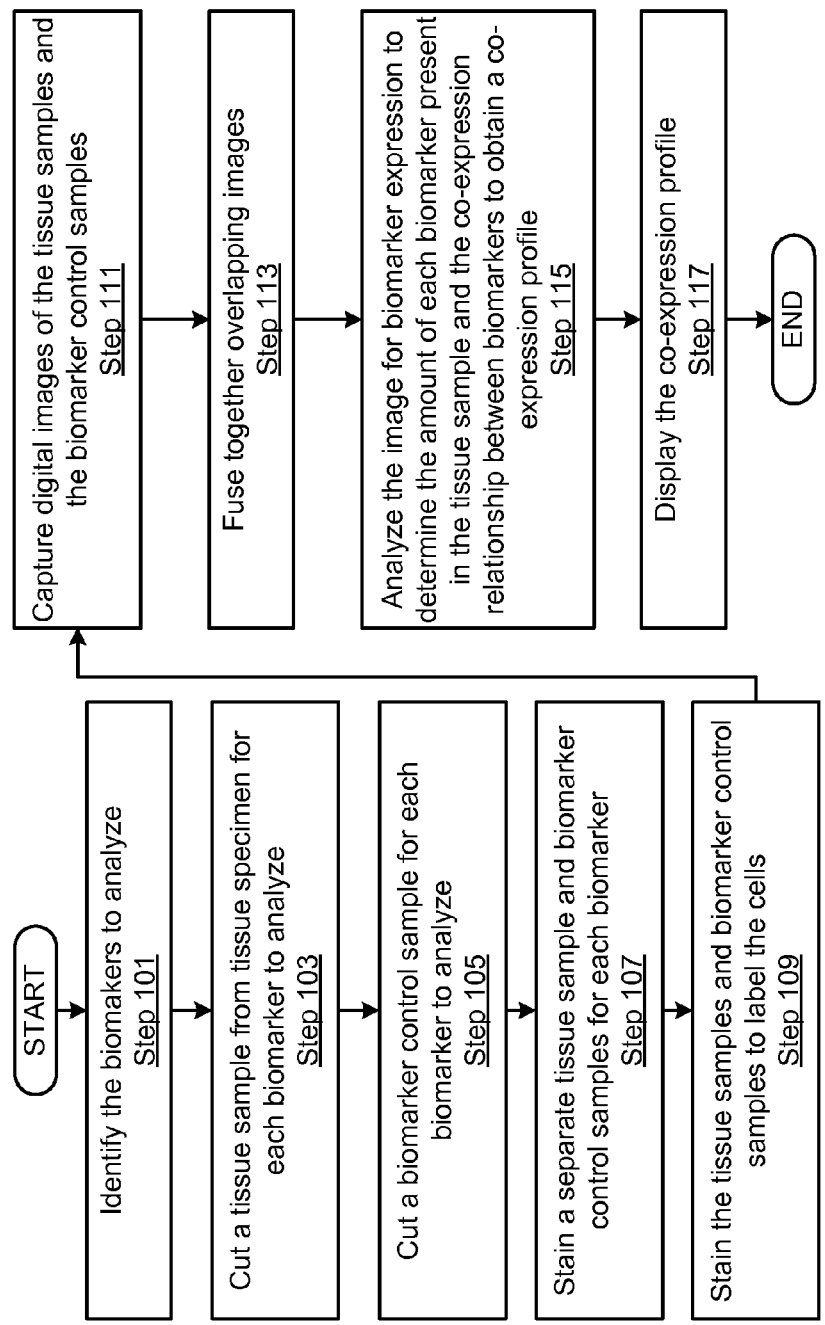
FIG. 1 shows a flowchart in accordance with one or more embodiments of the invention.

Specific embodiments of the invention will now be described in detail with reference to the accompanying Figures. Like elements in the various Figures are denoted by like reference numerals for consistency.

In the following detailed description of embodiments of the invention, numerous specific details are set forth in order to provide a more thorough understanding of the invention. However, it will be apparent to one of ordinary skill in the art that the invention may be practiced without these specific details.

In other instances, well-known features have not been described in detail to avoid unnecessarily complicating the description.

In general, embodiments of the invention relate to identifying a patient-specific biomarker profile. In one or more embodiments of the invention, the biomarker profile includes the co-expression relationships between the biomarkers in a patient's tissue sample. Specifically, embodiments of the invention examine co-expression of biomarkers on a per-cell basis within a tissue or cell preparation sample. Thus, embodiments of the invention identify when two or more biomarkers are present in the same cell or cells. The biomarkers may include, for example, amino acid, peptide, protein, nucleic acid, RNA, DNA, sugar, etc, or portions or combinations thereof.

In one or more embodiments of the invention, neighboring tissue sample layers are obtained from a tissue sample. The neighboring tissue sample layers intersect the same physical cells in accordance with one or more embodiments of the invention. In one or more embodiments of the invention, a single biomarker is analyzed per tissue-sample layer. Embodiments of the invention overlay or stack of the tissue sample layers in a post processing step to identify the co-expression between the layers of the cell in the biomarker profile. Thus, embodiments of the invention correlate single biomarker expressions on slices of individual cells to obtain a per-cell breakdown of multiple biomarker expressions.

In one or more embodiments of the invention, inherent error associated with tagging multiple biomarkers on the same sample is eliminated or minimized by first tagging biomarkers separately on separate slices, and then performing the co-expression analysis on a per-cell basis.

FIG. 1 provides an overview for performing biomarker analysis in accordance with one or more embodiments of the invention. In Step 101, the number of biomarkers to analyze is identified. In Step 103, a tissue sample is cut from a tissue specimen for each of the biomarkers in accordance with one or more embodiments of the invention. Obtaining a tissue sample is discussed below and in FIG. 2, reference 204 and 30.

In Step 105, biomarker control samples are cut from standard biomarker control cells. In one or more embodiments of the invention, the amount of each biomarker in the standard biomarker control cells is known prior to performing the biomarker analysis. The biomarker control samples may be placed on individual slides in accordance with one or more embodiments of the invention. Obtaining biomarker control samples is discussed below and in FIG. 2, reference 208 and 30.

In Step 107, the tissue samples and biomarker control samples are stained for biomarker expression. In one or more embodiments of the invention, each tissue sample is stained for a single biomarker so that cells expressing the biomarker are identifiable. Further, biomarker control samples are stained for the biomarker corresponding to the biomarker control sample. Staining the tissue sample is discussed below and in FIG. 2, reference 30.

In Step 109, the tissue samples and biomarker control sections are stained with an additional stain to label the cells so that individual cells are identifiable in accordance with one or more embodiments of the invention. The additional stain may be to stain the cytoplasm or membrane (i.e., outer border) of each cell of interest to facilitate segmenting these cells and distinguishing them from other non-relevant cells that may also be present in the same sample. Specifically, multiple cells of heterogeneous types (e.g., blood vessel cells, fibroblast cells, etc.) may exist within each tissue sample. In one or more embodiments of the invention, the additional stain distinguishes the cells of the specific type being studied from the cells of the type that are not being studied. The stain may be, for example, a generic histology stain that stains all cell nuclei blue. Step 109 may be performed, for example, to simplify subsequent identification and segmentation of the cells being assayed. In one or more embodiments of the invention, the additional stain is only applied when cell-based analysis is performed as discussed below with reference to FIG. 5. When pixel-based analysis is performed, the additional stain may not be applied in accordance with one or more embodiments of the invention.

In Step 111, digital images are captured of the stained tissue samples and the stained biomarker control section. Digital image creation is discussed below and in FIG. 2, reference 40.

In Step 113, overlapping captured images may be combined together into a single fused image in accordance with one or more embodiments of the invention. Specifically, multiple images corresponding to a single tissue sample are fused together so as to accurately portray the tissue sample on the slide.

In Step 115, the image is analyzed for biomarker expression to determine the amount of each biomarker present in the tissue sample of interest. In one or more embodiments of the invention, the analysis is performed by comparing the amount of staining of each biomarker on the image with the amount of staining present in the biomarker control images.

Further, the analysis of the image includes a co-expression analysis. The co-expression analysis identifies the relationship between biomarkers of cells present in the multiple images. Specifically, cells present in multiple images are identified and may be used to create a three dimensional image from the tissue sample images, whereby each layer of the three dimensional image is stained for a different biomarker. Thus, cells that have multiple biomarkers present or have no biomarkers present are identified. The result of performing an analysis is a co-expression profile. The co-expression profile describes the amount of overlap between the biomarker expression levels of different biomarkers in accordance with one or more embodiments of the invention. Performing the co-expression analysis is discussed below and in FIG. 2, reference 50.

In Step 117, the co-expression profile is displayed. The co-expression profile may be used to determine a treatment plan for a patient, to perform research, or to do other tasks.

Further, in one or more embodiments of the invention, the co-expression profile may be stored. For example, the analysis result may be stored in a data repository (e.g., a database, a file, a file system, etc.).

The following provides an example of performing the co-expression analysis when a tissue specimen is analyzed for three biomarkers. Although the following description is discussed with reference to three biomarkers, the analysis may be performed with more or less biomarkers without departing from the scope of the invention.

Figure 2:
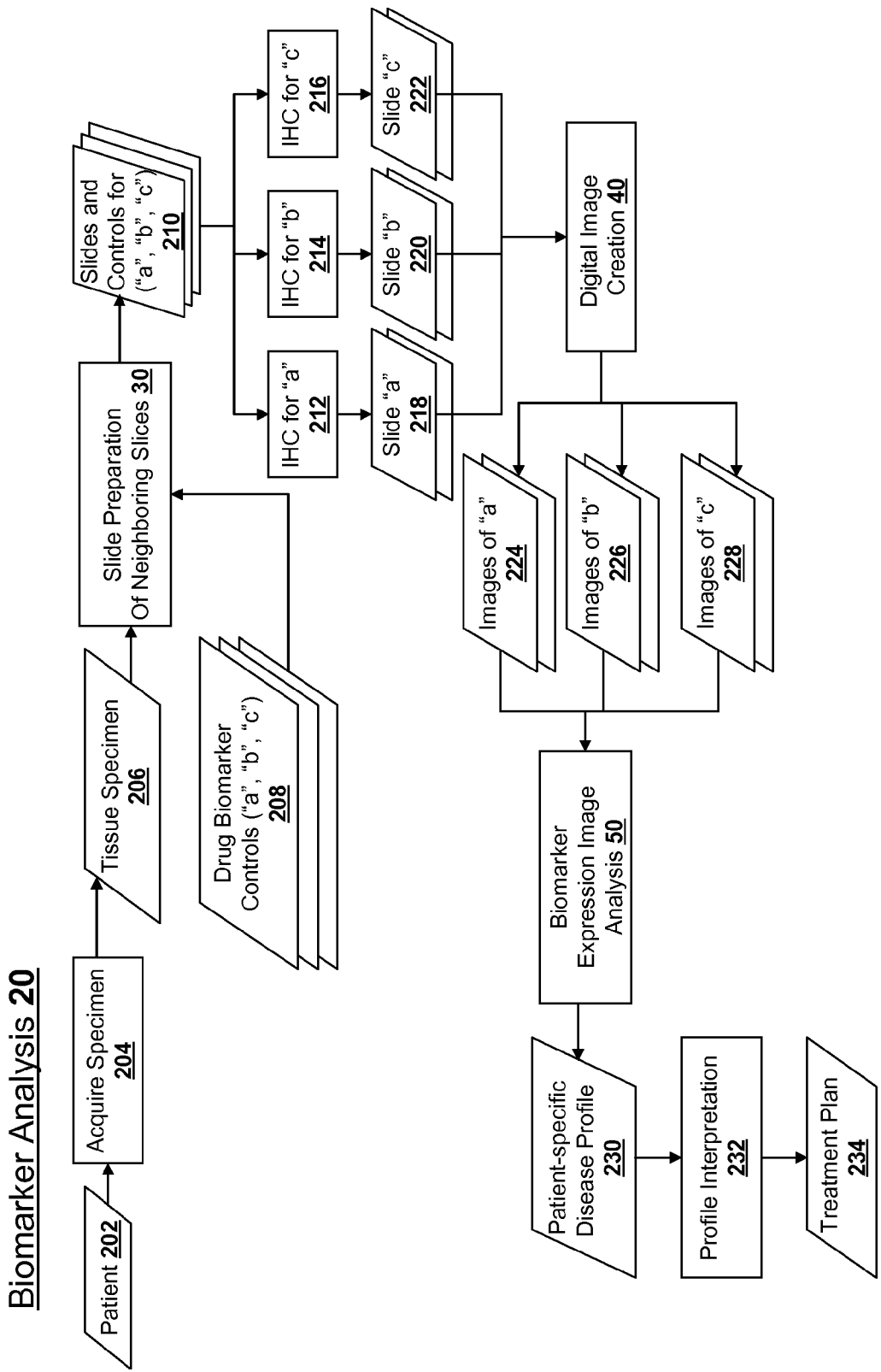
FIG. 2 shows a flow diagram for performing biomarker analysis in accordance with one or more embodiments of the invention.

FIG. 2 shows a flow diagram for performing biomarker analysis (20) in accordance with one or more embodiments of the invention. Specifically, FIG. 2 provides an overview of performing the biomarker analysis (20) for three biomarkers. Individual steps of FIG. 2 are discussed in more detail below with reference to FIGS. 3-5.

As shown in FIG. 2, a tissue specimen (206) is obtained (204) from a patient (202) in accordance with one or more embodiments of the invention. For example, the tissue specimen (206) may be obtained from a tumor affecting a specific site or organ of a patient. Alternatively, the tissue specimen may be obtained by growing cell lines in a culture. Obtaining the tissue specimen (204) may be accomplished using techniques known in the art.

In one or more embodiments of the invention, the tissue specimen (206) is prepared (30) to create resulting slides (210). The preparation (30) of the tissue specimen (206) is discussed below and in FIG. 3. Continuing with FIG. 2, the resulting slides (210) have thinly sliced layers of tissue samples from the tissue specimen (206). Each thinly sliced tissue sample layer neighbors one another in the source tissue specimen (206) obtained from the patient (202). In one or more embodiments of the invention, the tissue sample layers are sufficiently thin so that individual cells are sampled across multiple collected slices used in the analysis. In one or more embodiments of the invention, most of the individual cells are sampled across all of the slides, such that each slide includes a portion of each cell.

In one or more embodiments of the invention, each slide is stained (30) to identify a separate single biomarker (e.g., 212, 214, 216). For example, the first slide may be stained for biomarker 'a' (212), the second slide may be stained for biomarker 'b' (214), a third slide may be stained for biomarker 'c' (216), etc. Specifically, the tissue-sample layer on each slide is stained to create a stained tissue sample layer. Only one stain corresponding to a biomarker is applied to each slide in accordance with one or more embodiments of the invention.

Further, each tissue sample slide is prepared with a companion biomarker control slide (208) having known biomarker expression in accordance with one or more embodiments of the invention. In one or more embodiments of the invention, the biomarker control slides (208) are obtained from biomarker control cells. Accordingly, the slide preparation and staining produces a set of slides (210) where each tissue specimen has been prepared along with a control specimen and has been affixed to glass slides. Using IHC, antibodies and color tags for biomarkers "a" (212), "b" (214) and "c" (216) are applied to sections "a" (218), "b" (220) and "c" (222), respectively.

Digital images (e.g., 224, 226, 228) of each of the stained slides having the stained tissue sample layers and the stained biomarker control samples are created (40) in accordance with one or more embodiments of the invention. Capturing the digital images (e.g., 224, 226, 228) may be performed as discussed below and in FIG. 4.

The digital images (e.g., 224, 226, 228) are analyzed during biomarker expression image analysis (50) in order to determine the co-expression correlation at a cellular level. In one or more embodiments of the invention, the biomarker expression image analysis may be performed by image analysis software executing on a computer system. Analyzing the digital images (e.g., 224, 226, 228) may be performed, for example, as discussed below and in FIG. 5. In one or more embodiments of the invention, the result of the analysis is a patient-specific biomarker profile (230) that uses cell-centric multi-biomarker co-expression information in regard to biomarkers. Thus, a treatment plan (234) may be formulated by interpreting (232) the patient specific disease profile (230).

Figure 3:
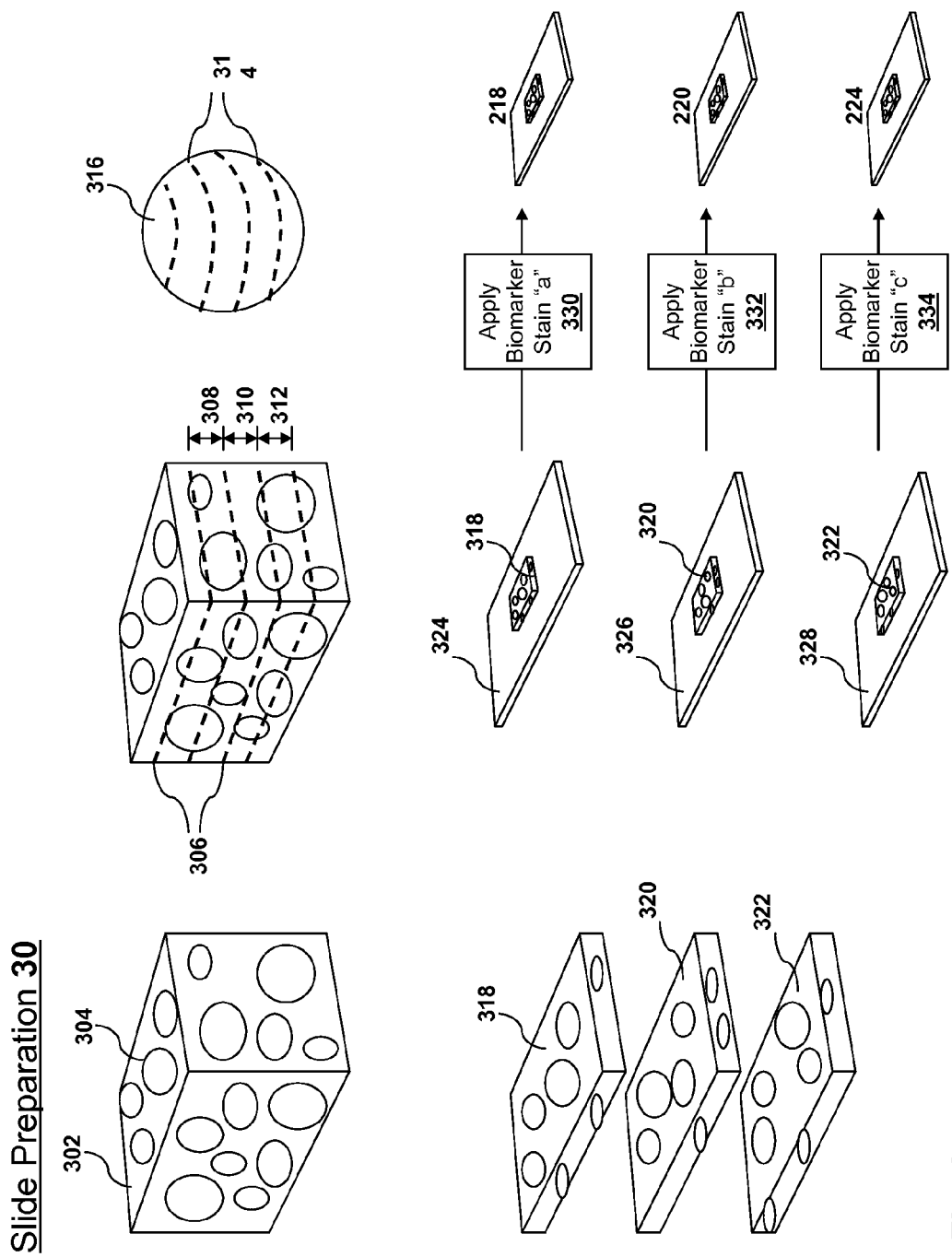
FIG. 3 shows a flow diagram for slide preparation in accordance with one or more embodiments of the invention.

FIG. 3 shows a flow diagram for slide preparation (30) in accordance with one or more embodiments of the invention. In one or more embodiments of the invention, the slide preparation (30) shown in FIG. 3 enables multi-layer neighbor analysis yielding multi-biomarker co-expression. Initially, a tissue specimen (302) having cells (304) is sliced uniformly (306) to create the tissue sample layers (318, 320, 322). The slicing is performed such that the resulting thickness of each tissue sample layer (e.g., 308, 310, 312) is equal. Those skilled in the art will appreciate that the equality between the resulting thicknesses of different tissue same layers may have a margin of error. Further, the slicing process partitions a single cell (316) into multiple sections (314) where each section (314) is in a different tissue sample layer (e.g., 318, 320, 322). Because of random variation of cells in the layers, not all cells will co-exist within each layer in accordance with one or more embodiments of the invention. However, decreasing the thickness of the slices may improve the likelihood of any given cell being represented in each tissue sample layer.

Continuing with FIG. 3, the tissue sample layers (e.g., 318, 320, 322) are placed on glass slides (e.g., 324, 326, 328, respectively). Each slide (e.g., 324, 326, 328, respectively) is subsequently stained (330, 332, 334) for a single biomarker.

In one or more embodiments of the invention, the staining uses the Immunohistochemistry (IHC) method, which results in applying a stain, such as brown for example, to cells containing the biomarker of interest. The same method may be used for different types of biomarkers and diseases, such as inflammatory and metabolic diseases in accordance with one or more embodiments of the invention. Using the IHC methodology, a specific antibody that binds to the biomarker of interest is applied to a thin slice of the tissue sample. A color label is applied to the thin slice to tag the antibody. As a result, positive cells having the biomarker of interest has a distinctive color the intensity of which correlates to the level or abundance of the specific biomarker in the cell. Conversely, negative cells that do not express the biomarker are either not stained or do not have the same intensity of staining as the positive cells having the biomarker of interest. The result of the staining yields sections of tissue sample (218, 220, 224) which have each been stained for a single biomarker.

Figure 4:
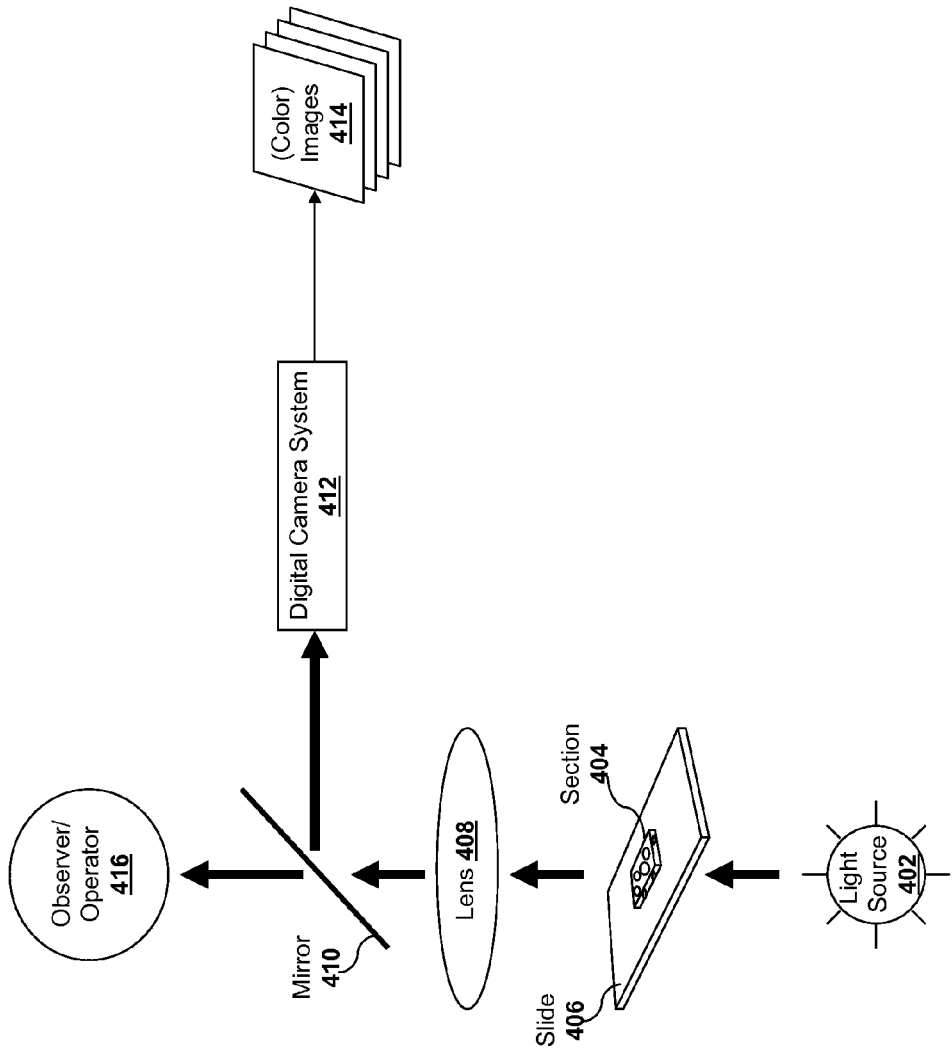
FIG. 4 shows a flow diagram for obtaining digital images in accordance with one or more embodiments of the invention.

FIG. 4 shows a flow diagram for creating digital images in accordance with one or more embodiments of the invention. In one or more embodiments of the invention, the digital images is created using a microscope and a camera. Specifically, the digital camera may be attached to the microscope. In alternative embodiments, the digital camera is a part of the microscope. The microscope may be standard microscope with high quality objectives (i.e., lenses).

In order to capture the digital images (e.g., 224, 226, 228), an operator may examine the stained slides under the microscope to capture digital images of each slide specimen. Alternatively, all slides may be scanned and slightly overlapped images from the entire slides are captured and stitched to form one large image for each entire slide, using an unattended automated slide capture device.

The capturing of a digital image may be performed by shining a light source (402) through the stained tissue sample layer (404) affixed to slide (406). The light source, for example, may correspond to a light bulb. A lens system (408) focuses the refracted light which is observed by an operator (416) and/or reflected by a mirror (410) to a digital camera (412). The digital camera (412) converts the observed light into digital images (414) that may then be analyzed by image analysis software. The digital images (414) may correspond to color images or grayscale images in accordance with one or more embodiments of the invention.

Additionally, in one or more embodiments of the invention, digital images are captured of a blank region of each slide devoid of cells or tissue elements for later use to perform light and/or shading correction control. Consecutive slightly overlapping images covering all of the cells of interest in section of tissue sample or cell reparation may also be captured. Images may be captured in any format that is usable by subsequent software algorithms in accordance with one or more embodiments of the invention. Accordingly, the digital images may be sent to a computer system, which may or may not be attached to or a part of the digital camera, for analysis by analysis software.

Figure 5:
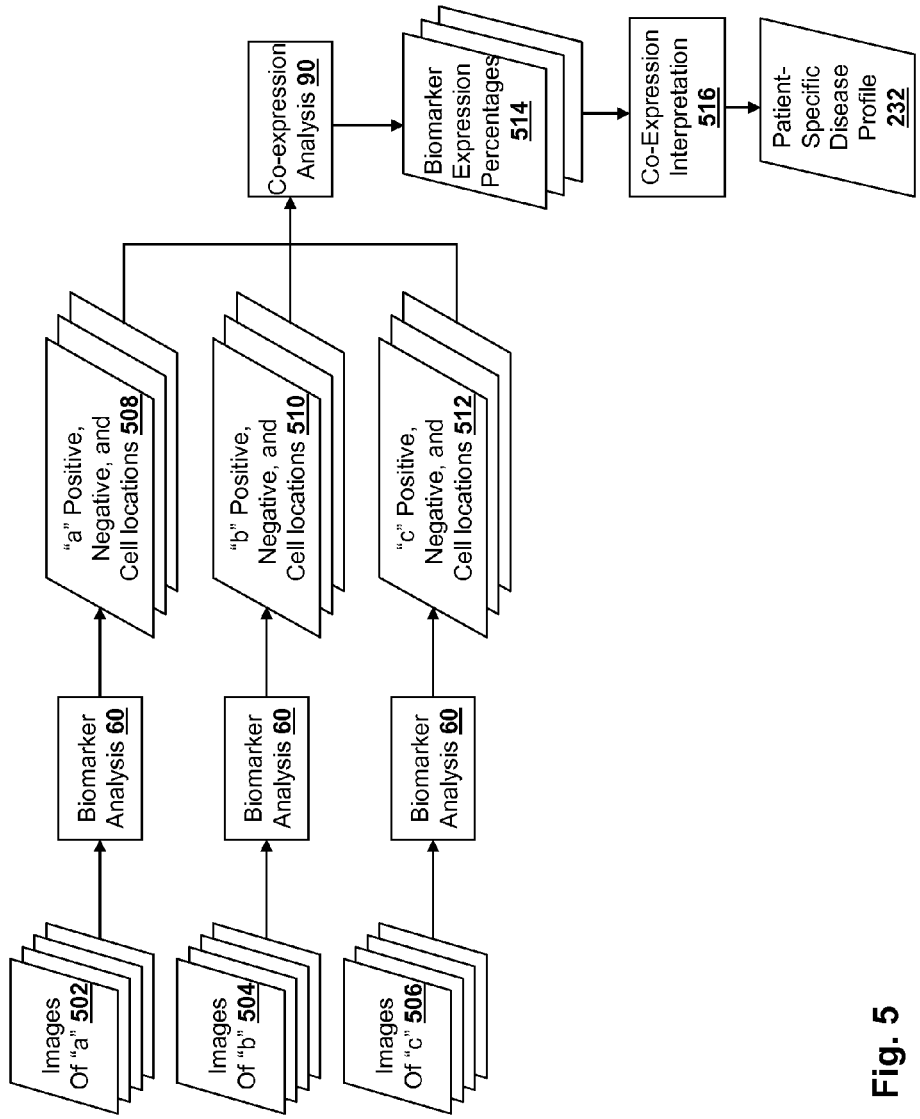
FIG. 5 shows a flow diagram for a multiple biomarker expression method in accordance with one or more embodiments of the invention.

FIG. 5 shows a flow diagram for biomarker expression image analysis (50) in accordance with one or more embodiments of the invention. Individual steps of FIG. 5 are discussed in more detail below and with reference to FIGS. 6 and 9. Returning to FIG. 5, the analysis discussed below is in reference to a cell-based analysis. Alternatively, a pixel-based analysis may be performed. In a pixel-based analysis, rather than counting the number of cells that have the presence or lack thereof of a biomarker, individual pixels are counted.

Returning to the discussion of the cell-based analysis, as shown in FIG. 5, each digital image (e.g., 502, 504, 506) is analyzed using the biomarker analysis (60) (discussed below and in FIG. 6) to identify the cells that test positive for a particular biomarker, the cells that test negative for the particular biomarker, and to identify the spatial location of each cell. The spatial location of each cell may be represented as a surrounding polygon in image-pixel space and maintains a representation of which image pixels are contained therein. As discussed above, because cells are stained with additional stains when cell based analysis is performed, individual cells are identifiable.

Figure 9:
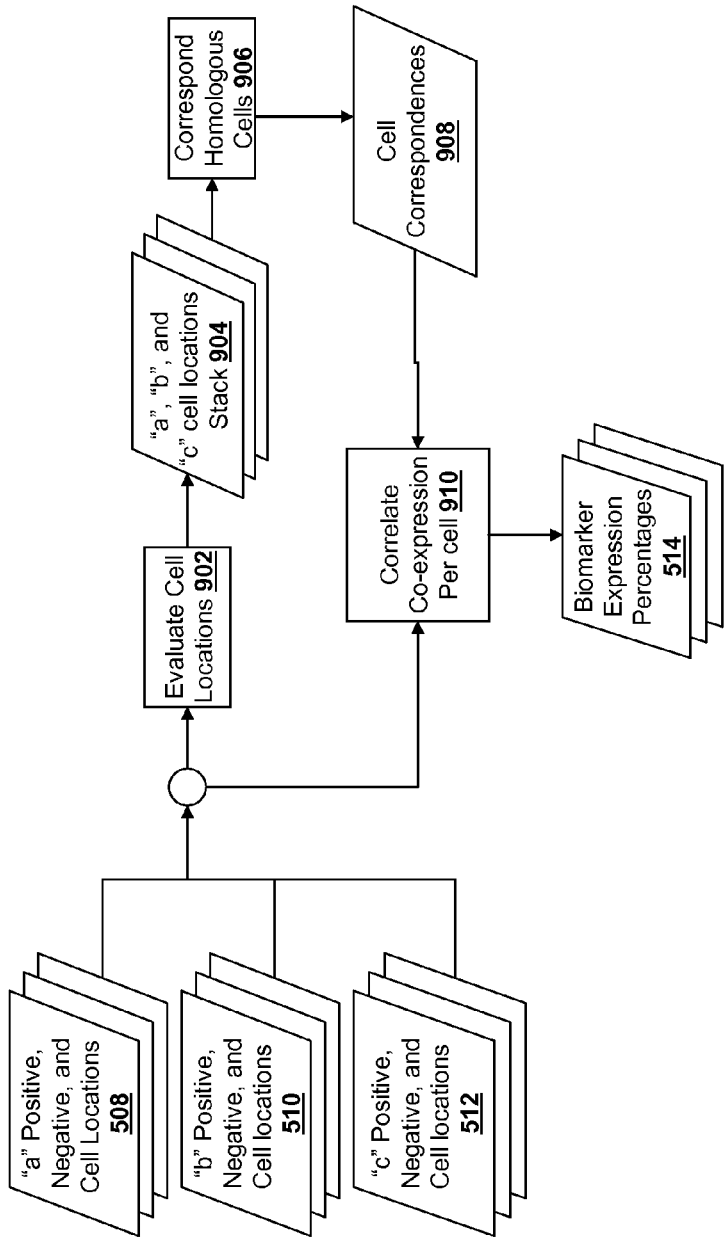
FIG. 9 shows a flow diagram for performing co-expression analysis in accordance with one or more embodiments of the invention.

Continuing with FIG. 5, spatial expression information (508, 510, 512) is stacked or overlaid onto one another during co-expression analysis (90) to determine co-expression information (514) specifying co-expression relationships on a per-cell basis. Specifically, the co-expression information (514) identifies, for each cell, the biomarkers in the cell. Further, the co-expression information (514) identifies the percentage of cells that include each subset of biomarkers (e.g., the subsets of {'a'}, {'a', 'b'}, {'a', 'c'}, {'a', 'b', 'c'}, {empty}, etc.). FIG. 9 shows how the processing may be performed to stack or overlay the images on each other to identify the co-expression relationships in accordance with one or more embodiments of the invention.

Continuing with FIG. 5, the co-expression information (514) is interpreted (516) to devise a patient-specific biomarker profile (232), which includes more accurate information pertaining to the interrelationships of multiple drug target classes. Specifically, interpreting the co-expression information includes identifying different subsets of biomarkers in which each cell has at least one biomarker in the subset. For example, if biomarkers 'x' and 'y' are present in 60% of the cells, and biomarkers 'y' and 'z' are present in the remaining 40% of the cells, then the patient-specific biomarker profile may include {'x', 'z'} and {'y'} because 'x' and/or 'z' are present in 100% of the cells and 'y' is present in 100% of the cells.

Figure 6:
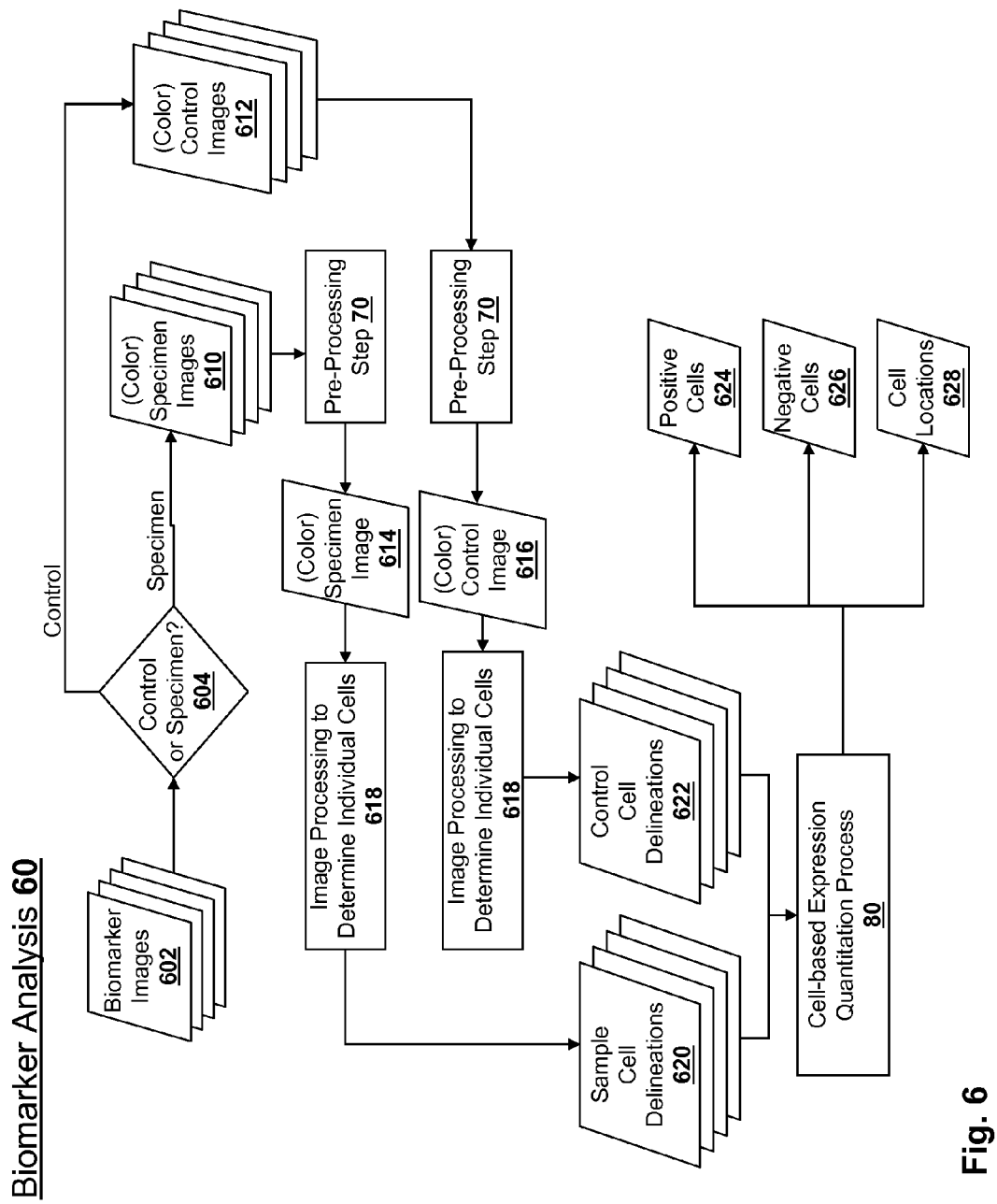
FIG. 6 shows a flow diagram of a biomarker analysis method in accordance with one or more embodiments of the invention.

FIG. 6 shows a flow diagram of a biomarker analysis method (60) in accordance with one or more embodiments of the invention. Specifically, FIG. 6 provides detail regarding the biomarker analysis (60) discussed above and in FIG. 5. As discussed above, the biomarker analysis uses the digital images (602) as input in accordance with one or more embodiments of the invention. Specifically, each biomarker has an image corresponding to a stained tissue sample layer and an image corresponding to a stained biomarker control cells.

In one or more embodiments of the invention, images (602) are divided (604) into a sample image set (610) (i.e., images corresponding to stained tissue sample layers) and biomarker control image set (612) (i.e., images corresponding to a stained biomarker control standard). The image sets (e.g., sample image set (610), biomarker control image set (612)) are pre-processed (70) in accordance with one or more embodiments of the invention. In one or more embodiments of the invention, the pre-processing step (70) color balances images and/or combines images together to form a single specimen image (614) and single biomarker control image (616) from a set of multiple images. Combining the images may be performed when a single image captured through a high magnification microscope lens does not capture all cells of interest in a slice of tissue sample. In such a situation, a set of images is taken to represent different areas of the same slide to include most, if not all, the cells of interest and the set is combined to create the single image of the slide. The pre-processing of images is discussed in greater detail below and in FIG. 7.

Continuing with FIG. 6, the single sample image (614) and the single biomarker control image (616) are processed (618) to identify sample cell delineation information (620) and biomarker control cell delineation information (622). The processing of the single sample image (614) and the single biomarker control image (616) may be performed using techniques known in the art.

The sample cell delineation information (620) is information that identifies individual cells within the sample cell images. Specifically, the sample cell delineation information (620) specifies each cell as distinct from other cells in the sample cell images. Similarly, the biomarker control cell delineation information (622) is information that identifies individual cells within the biomarker control images. For example, the sample cell delineation information (620) and the biomarker control cell delineation information (622) may be stored by describing each cell using a polyline, polygon, set of pixels, and/or other information that identifies which image pixels correspond to individual cells. The sample cell delineation information (620) and the biomarker control cell delineation information (622) further includes information regarding the coloring of each pixel in the single sample image (614) and the single biomarker control image (616) in accordance with one or more embodiments of the invention.

In one or more embodiments of the invention, the sample cell delineation information (620) is analyzed to identify quantitative biomarker expression levels on a per-cell basis (80) using the biomarker control cell delineation information (622). The analysis of the sample cell delineation information to identify quantitative biomarker expression levels on a per-cell basis (80) using the biomarker control cell delineation information (622) is discussed below and in FIG. 8. The results of the analysis discussed below and in FIG. 8 may include identification of cells that are positive (624), cells that are negative (626), and spatial location information for each cell (628). The results may be available if a cutoff value that distinguishes positive expression level (i.e., amount of stain that indicates a positive expression level) from negative expression level (i.e., lack of stain that indicates a negative expression level) has been previously determined and provided to the computer software. If a cutoff value is not provided, the results of the analysis may identify the biomarker expression level in each cell using, for example, graphing schemes and/or tables.

Alternatively, rather than using a cutoff value, a continuous scale of expression levels may be defined for the biomarkers using the biomarker control images. Relative to the continuous scale, the expression level of the biomarkers in the tissue sample may be defined. For example, if the control sample expression level of a biomarker is said to be 100 units, the levels of the biomarker in the tissue sample may be given for each cell in units ranging from 0-100, or higher, depending on how the level of color hue and intensity in each cell compare to the same in the control cells with a value of 100. In the example, if a cell in the tissue sample image show staining intensity that is half the intensity in the control image that has a predetermined value of 100, then the cell in the sample image may be assigned a numerical expression level for the first biomarker of 50.

Figure 7:
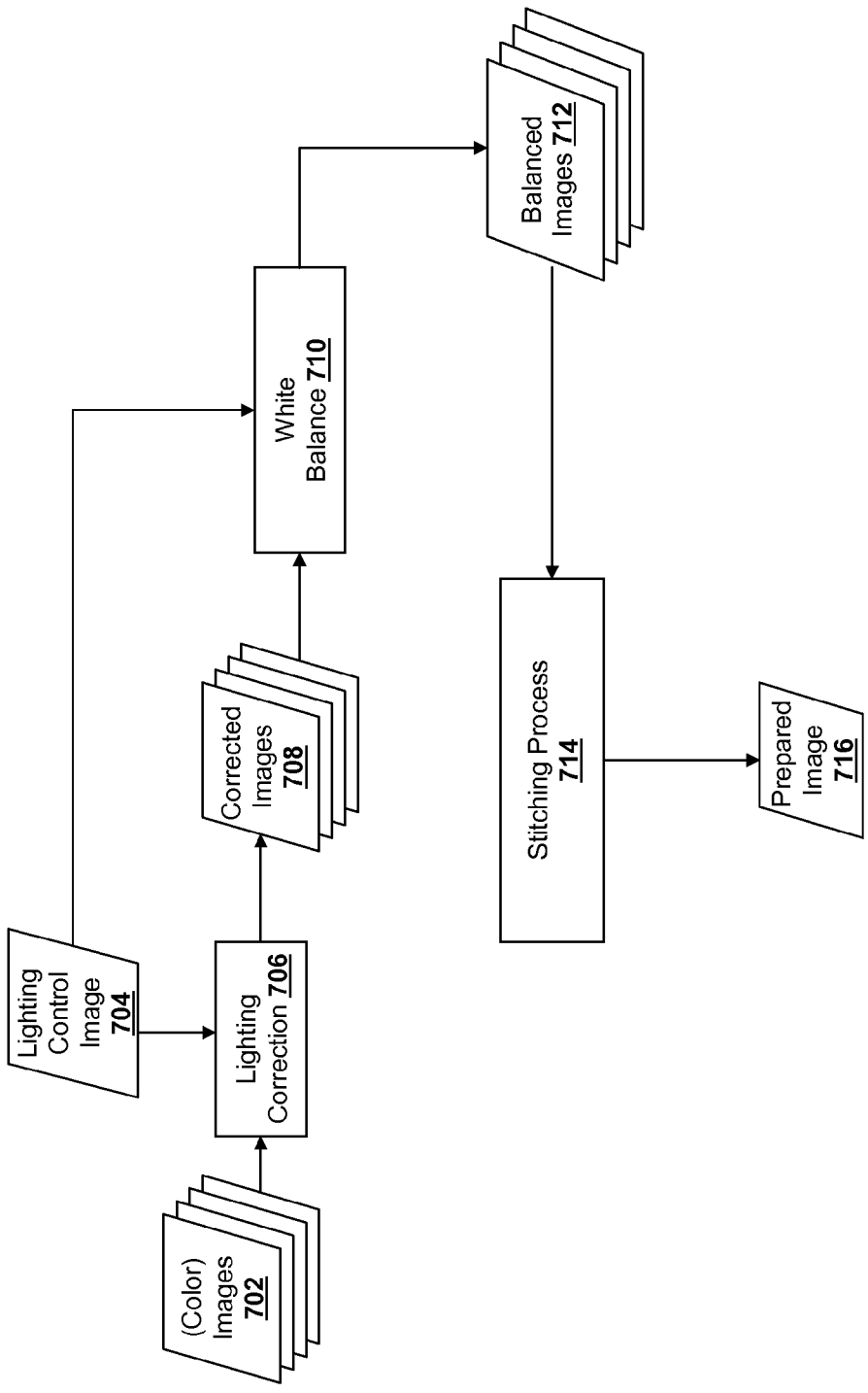
FIG. 7 shows a flow diagram for preprocessing the images in accordance with one or more embodiments of the invention.

FIG. 7 shows a flow diagram for preprocessing the images (70) in accordance with one or more embodiments of the invention. Specifically, FIG. 7 provides detail regarding the pre-processing step discussed above and in FIG. 6. In one or more embodiments of the invention, the pre-processing step (70) is performed separately for each set of images (702). Specifically, the pre-processing step (70) is performed for the tissue sample images, and a separate pre-processing step (70) is performed for the biomarker control images.

In one or more embodiments of the invention, the preprocessing step includes light correction (706) of the set of images (702). In one or more embodiments of the invention, the light correction (706) removes uneven lighting or shading artifacts. The lighting correction may be performed, for example, when the images are captured at less than 40× microscope objective (lens). However, lighting correction may be performed when the images are captured greater or equal to a 40× microscope objective in accordance with one or more embodiments of the invention.

As discussed above, the correction may include using a lighting control image (704) captured of the blank part of the slide devoid of cells when the sample images (702) were captured. Because the lighting control image (704) is a digital image captured from the slide, the lighting control image (704) shows light variation as seen through the microscope used to capture the sample images. For example, the lighting control image may capture a mostly white image having a brighter area in the center which darkens slightly near the edges of the viewable field. In alternative embodiments of the invention, the light correction (706) is not performed.

In one or more embodiments of the invention, the corrected images (708) are white-balanced (710) to produce balanced images (712). In one or more embodiments of the invention, the white balance (710) is performed using the lighting control image (704). In one or more embodiments of the invention, white balancing ensures that color information is accurately represented.

In one or more embodiments of the invention, the balanced set of images captured from different areas from each slide (712) undergo a stitching process (714) such that a single large image can be created to represent each slide. The stitching process (714) identifies the overlapping image regions in two or more images captured from adjacent areas of the slide. Based on the overlapping regions, the stitching process (714) may fuse the images into a single image (716). Thus, the single image (716) may show the entire tissue sample on a single slide.

In one or more embodiments of the invention, the stitching (714) is optional. Specifically, rather than performing the stitching process (714) the biomarker analysis discussed in FIG. 6 may use multiple images. However, for multi-marker analysis on sections that are too large to be captured in one image, stitching images that capture the entire area of interest in a slide is important to ensure accurate spatial information and correlation with cells on the adjacent slices, and to ensure cells are not counted more than once.

Figure 8:
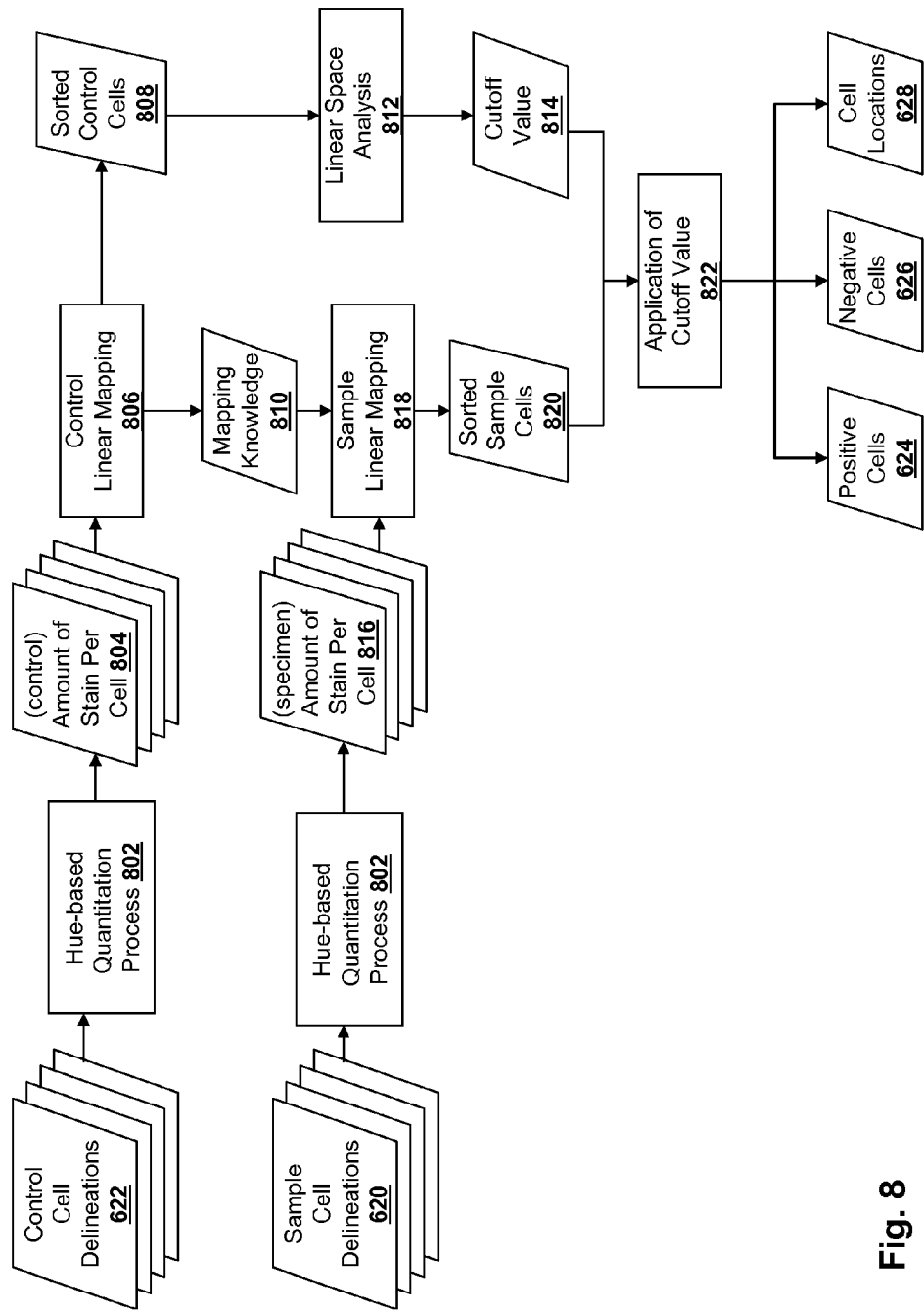
FIG. 8 shows cell-based expression analysis in accordance with one or more embodiments of the invention.

FIG. 8 shows cell-based expression analysis (80) in accordance with one or more embodiments of the invention. As shown in FIG. 8, the input to the cell-based expression analysis may include biomarker control cell delineation information (622) and the sample cell delineation information (620). In one or more embodiments of the invention, the control cell delineation information (622) is processed first to calibrate the processing of the sample cell delineation information (620).

Biomarker control cell delineation information (622) is processed (802) to identify the amount of stain bound to the biomarker of interest. The process of analyzing the control cells may include user guidance to aid in determining the hue or color representation for positive and/or negative cells.

The processing of the control cell delineation information (622) results in quantitative biomarker expression levels defining an amount of stain for each control cell (804). The quantitative biomarker expression levels for the control cells are used to perform a control linear mapping (806) that creates sorted control cells (808) for further processing. Specifically, the control linear mapping sorts the control cells according to the quantitative biomarker expression levels. Thus, cells that have low levels of staining are on one end of the sorted control cells (808) while cells that exhibit high levels of staining are on another end of the sorted control cells. Thus, the linear mapping relates color information for images in color, or grayscale information for images in grayscale, with the biomarker expression level of the control cells.

To perform the processing, the sorted control cells may then be analyzed (812) in regard to the known expression levels for the biomarker control to provide the cutoff value (814). As discussed above, the cutoff value distinguishes the amount of stain required to separate cells that are positive from cells that are negative for a corresponding biomarker. Specifically, because the control slide has positive cells that have known high amounts of a specific biomarker, negative cells, and cells that have intermediate amount of the biomarker, a linear control curve can be used to determine the amount of stain (biomarker) in a tissue sample cell to indicate that a cell is positive for the specific biomarker, a cell is negative for the specific biomarker, and the amount of stain in the cell that represents various intermediate quantities of each biomarker. Alternatively, a control slide may lack cells with intermediate biomarker expression level.

In one or more embodiments of the invention, after determining the cutoff value in the linear cell space, the sample cell delineation information (620) is analyzed using hue analysis (802) to determine the quantitative expression level defining the amount of stain of each cell (816). Specifically, the quantitative expression level is a value representing the amount of stain on each cell based on the hue of the cell in the sample cell delineation information (620). The amount of stain for each cell (816) is mapped (818) for each cell to create sorted sample cells (820) in accordance with one or more embodiments of the invention.

In one or more embodiments of the invention, the cutoff value (814) is applied (822) to the sorted sample cells (820) to define whether each sample cell is positive (624) or negative (626) for a specific biomarker. Specifically, if the biomarker expression level for a cell is in the region defined by the cutoff value as negative, then the cell is determined to be negative for the specific biomarker. Conversely, if the biomarker expression level for a cell is in the region defined by the cutoff value as positive, then the cell is determined to be positive for the specific biomarker. Furthermore, cell location and delineation information (628) for each sample cell (620) is retained throughout this processed and provided as output for use in subsequent processes. Although the above discusses the use of linear analysis, non-linear analysis may be used without departing from the scope of the invention. Accordingly, as a result of the cell-based expression analysis (80), the positive cells (624), negative cells (626), and cell locations (628) are identified.

FIG. 9 shows a flow diagram for performing co-expression analysis (90) in accordance with one or more embodiments of the invention. Specifically, FIG. 9 and the description below provides a description of the co-expression analysis introduced above with respect to FIG. 5. Continuing with FIG. 9, in one or more embodiments of the invention, the co-expression analysis identifies the overlap of biomarkers present in the same cell.

In one or more embodiments of the invention, the input to the flow diagram of FIG. 9 is information sets (508), (510), and (512) corresponding to each biomarker being analyzed. As discussed above, the input may be obtained from the biomarker analysis performed in FIG. 6 in accordance with one or more embodiments of the invention. Also, as discussed above, although only three biomarkers are examined, the described method could easily be modified by someone skilled in the art to include more or less biomarkers.

Continuing with FIG. 9, each information set includes cell spatial information as well as quantitative positive and negative expression information. Furthermore, each information set corresponds to a specimen layer that was cut from neighboring slices in the tissue sample as described in FIG. 3. Cell locations are evaluated (902). Specifically, the neighboring sample layers in the tissue sample specimen are stacked on one another using the information sets (508), (510), and (512). The evaluation may include performing registration, warping, and/or some alignment process to roughly align the spatial locations of cells to one another in regard to each neighboring slice. The alignment process may utilize standard rigid alignment, registration, warping, and morphing procedures. The alignment process may be performed automatically and/or may also involve user guided methods that depend on the operator specifying a plurality of points within each layer as being homologous to those on another layer. In one or more embodiments of the invention, the resulting stack (904) represents a rough alignment of cell locations and their accompanying biomarker expression levels.

The aligned stack (904) may be analyzed (906) to establish homology between every cell for every layer in the stack. In one or more embodiments of the invention, not every cell will be represented on all layers, thus process (906) may also includes criteria for determining which cells are incomplete and removes or otherwise prevents those cells from being processed by subsequent steps. The output of process (906) is a set of complete cell correspondences (908). In one or more embodiments of the invention, the cell correspondences indicate which cells are represented on all layers. The cell correspondences include biomarker expression information for each biomarker and each cell.

The co-expression is correlated on a per-cell basis (910) in accordance with one or more embodiments of the invention. Specifically, the correlation examines correspondence information (908) on a per-cell basis and determines whether the cell is positive or negative for all biomarkers of interest. The output (514) represents cell-centric biomarker expression percentages indicating which cells have only biomarker "a", which only have "b", which only have "c", which have "a" and "b" but not "c", which have "a" and "c" but not "b", which have "b" and "c" but not "a", which have "a", "b", and "c", and which cells have no biomarker expression in accordance with one or more embodiments of the invention.

Furthermore, the above method may be modified to include more or less biomarkers and subsequently modifying the reported percentages (514) based upon all possible combinations of biomarkers of interest. Thus, a physician may accurately determine the overlapping cell classes addressed by each drug in question. Although the analysis is simplified to show biomarker values as only positive or negative, expression of biomarkers can also be expressed on a continuous scale as 20, 30, 35, or 85 units, for example. Co-expression with continuous values may be shown using any graphing methods and/or table format as discussed below.

Display

The co-expression results may be displayed in many different forms. For example, expression data may be shown in a table, which includes correlated expression for each combination of biomarkers. For example, in the scenario in which three biomarkers, "a", "b", and "c", are analyzed, the tabulated data may indicate the percentage of cells containing, for example:

1) Biomarker "a" (and varying amounts of the others),
2) Biomarker "b" (and varying amounts of the others),
3) Biomarker "c" (and varying amounts of the others),
4) Only "a",
5) Only "b",
6) Only "c",
7) Both "a" and "b" but not "c",
8) Both "a" and "c" but not "b",
9) Both "b" and "c" but not "a"; and
10) "a", "b", and "c".

The above list is not exhaustive, but provides a general reporting mechanism that may be employed to create the patient-specific disease profile in regard to the biomarkers of interest.

Further, the above described categories of expression may be color coded so that cells within each category are colored on the captured/processed images enabling the operator to examine individual cells in regard to their physical location within the tissue sample. The cell-centric spatial correlation may further contribute to the patient-specific biomarker profile. In one particular embodiment of this color correlation, the displayed colors could be user controlled such that certain combinations or expressions can be turned on and off.

Further, in one or more embodiments of the invention, a user may interactively select different combinations of biomarkers of interest. The display may dynamically update the associated spatial rendering of correlated cells. The spatial rendering may use different colors to convey information in an effective manner. Furthermore, selected biomarker expression information may be displayed in tabulated form, graph form, on the captured image directly, etc.

In one or more embodiments of the invention, the display may allow the operator to select the biomarker that mediates action of the least toxic and most effective drug, then selecting all cells that are negative and to indicate what percentage of cells are positive for the target for the next drug of choice. Selecting negative cells for both can indicate what remaining cells are positive for another drug. This interaction can contribute to the biomarker profile interpretation (232) for establishing optimal drug combinations.

In one or more embodiments of the invention, interactive display may be used to correlate a biomarker mediating response to a specific treatment with that of apoptosis and/or proliferation. A graph, for example, may simultaneously indicate biomarker expression for cyclin A and cleaved caspase 3 and may show, for example, that only cells with having some particular expression level of biomarker X are negative for cycline A (a marker of cell proliferation) or positive for cleaved caspase 3 (a marker for apoptotic cell death).

The following is an example of co-expression analysis in accordance with one or more embodiments of the invention. In the following example, consider the scenario in which a doctor is treating a patient for colon cancer. Specifically, the doctor would like to determine which chemotherapy drugs to use to treat the patient. The presence of biomarker A in the patient's cancer cells indicates that the cells will response to drug A. The presence of biomarker B in the patient's cancer cells indicates that the cells will response to drug B.

Figure 10:
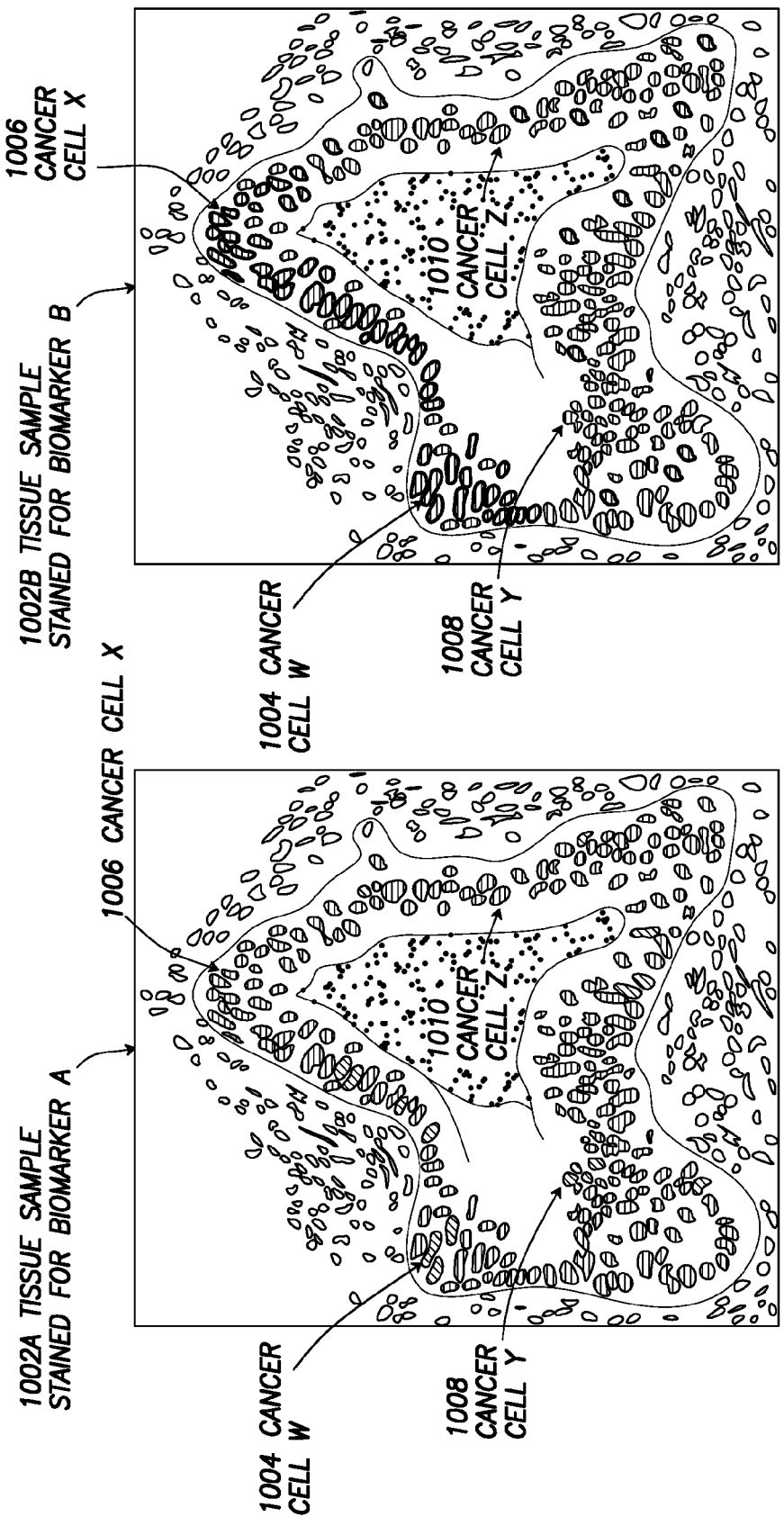
FIGS. 10A-10B show an example in accordance with one or more embodiments of the invention.

Continuing with the example, the doctor takes a tissue sample from the patient and sends the tissue sample to a lab. A lab technician obtains two thin layers from the tissue sample. FIGS. 10A and 10B show each layer in the example in accordance with one or more embodiments of the invention. Specifically, FIGS. 10A and 10B show a representation of an actual tissue section from human colon cancer. The representation of the actual tissue section shows a structure called a "gland" or "crypt" which has a central space (denoted with small black dots) and lined in a circular fashion by cancer cells that together form a deformed ring structure. As shown in the example, the lab technician slices the tissue sample such that many of the cells in the tissue sample are in both layers.

As shown FIG. 10A, the lab technician stains all nuclei of all cells blue.

Thus, all individual cells in the section are identifiable. Further, the lab technician through a multistep biomarker staining process adds a brown stain, which attaches to cancer cell nuclei positive for the biomarker A, to the tissue sample layer shown in FIG. 10A. Thus, as shown in 10A, cancer cells that are positive for biomarker A have brown staining (as shown by the hatch marks at a 45 degree angle in FIG. 10A). The remaining cells remain blue (as shown by the horizontal hatch marks in FIG. 10A).

Similarly, the lab technician stains the second layer for the second biomarker as shown in FIG. 10B. Specifically, the lab technician stains all nuclei of all cells blue. Further, the lab technician adds a brown stain, which attaches to cancer cell membranes (the outside wall of the cancer cell) positive for the biomarker B, to the tissue sample layer shown in FIG. 10B. Thus, as shown in 10A, cancer cells that are positive for biomarker B have brown staining on the edges (as shown by the thick border in FIG. 10B). Further, all cells have blue staining (as shown by the horizontal hatch marks in FIG. 10B).

For the purpose of clarity in the drawings, the blue staining of the nuclei is described as being performed prior to any other staining. However, the lab technician may typically perform the staining of the nuclei after performing staining for the respective biomarkers.

Continuing with the example, after simply looking at the slides individually, the person performing the analysis may believe that 50% of the cells are positive for biomarker A and 50% of the cells are positive for biomarker B. However, he or she may not know whether it is the same or different 50% that are positive for biomarkers A and B. For example, the person performing the analysis cannot say whether the 50% of cancer cells that have biomarker A are the same 50% of cancer cells that have biomarker B. If they are the same, then only one of the drugs may be used and a different treatment modality must be added to eliminate the remaining 50% of the cancer cells that do not express marker A or marker B (here 50%). However, if 50% of the cancer cells have biomarker A only and the other 50% have biomarker B only, then giving both drugs A and B is necessary to kill all cancer cells.

Accordingly, the person performing the analysis obtains digital images of both tissue sample layers. He or she then initiates the co-expression analysis using a computer system with the image analysis software. During the computerized analysis, the software overlays the tissue sample layers to identify the co-expression relationship between biomarker A and biomarker B. Specifically, the software is able to identify the certain cancer cells that are positive for both biomarker A and biomarker B (e.g., cancer cell W (1004)). Further, the computer system is able to identify the certain cancer cells that are positive for biomarker B, but not for biomarker A (e.g., cancer cell X (1006)). Additionally, the computer system is able to identify the certain cancer cells that are positive for biomarker A, but not for biomarker B (e.g., cancer cell Y (1008)). Finally, the computer system is able to identify the certain cancer cells that are negative for both biomarker A and biomarker B (e.g., cancer cell Z (1010)). Accordingly, the image analysis software provides to the person performing the analysis the percentages of cells in each of the categories (e.g., positive for both, positive for only biomarker A, positive for only biomarker B, and negative for both). A report with these findings is generated.

After reviewing the report, the doctor may determine that because some cancer cells will not respond to treatment with either drug A or drug B because they are negative for both biomarkers A and B, an additional drug should be used. Thus, with the report, the doctor may provide the right combination of chemotherapy drugs which combined activity kills most or all of the cancer cells, and withhold drugs that are not necessary, thereby saving the patient from toxic side effects.

Although the above is discussed using the IHC method, other methods may be used to stain cells without departing from the scope of the invention. For example, Silver In Situ Hybridization (SISH) can be used to tag the gene Her2 in sections of breast cancer tissue producing black dots in the nuclei of cancer cells. The number of black dots in each cell nucleus correspond to one copy of the Her2 gene. Another probe is used to label chromosome 17 on an adjacent tissue slice. When in a given cancer cell the number of Her2 copies exceeds the number of chromosome 17 copies this is called Her gene amplification. Breast cancers with amplified Her2 have worse prognosis, but also respond favorably to treatment that targets Her2. Thus, a tissue sample can be labeled with the Her2 DNA probe and a subsequent tissue sample may be labeled with the chromosome 17 probe. Both neighboring tissue samples may be stained with the SISH technique. The next subsequent tissue sample may be stained for ER using the IHC technique, while the next subsequent tissue sample may be stained for thymidylate synthase using the IHC technique. The image analysis can be used to determined which cells have Her2 gene amplification. Further, the percentage of cells, which do not have Her2 gene amplification, positive for ER may be determined. From the remaining cells, the percentage of cells positive for thymidylate synthase may be determined.

Figure 11:
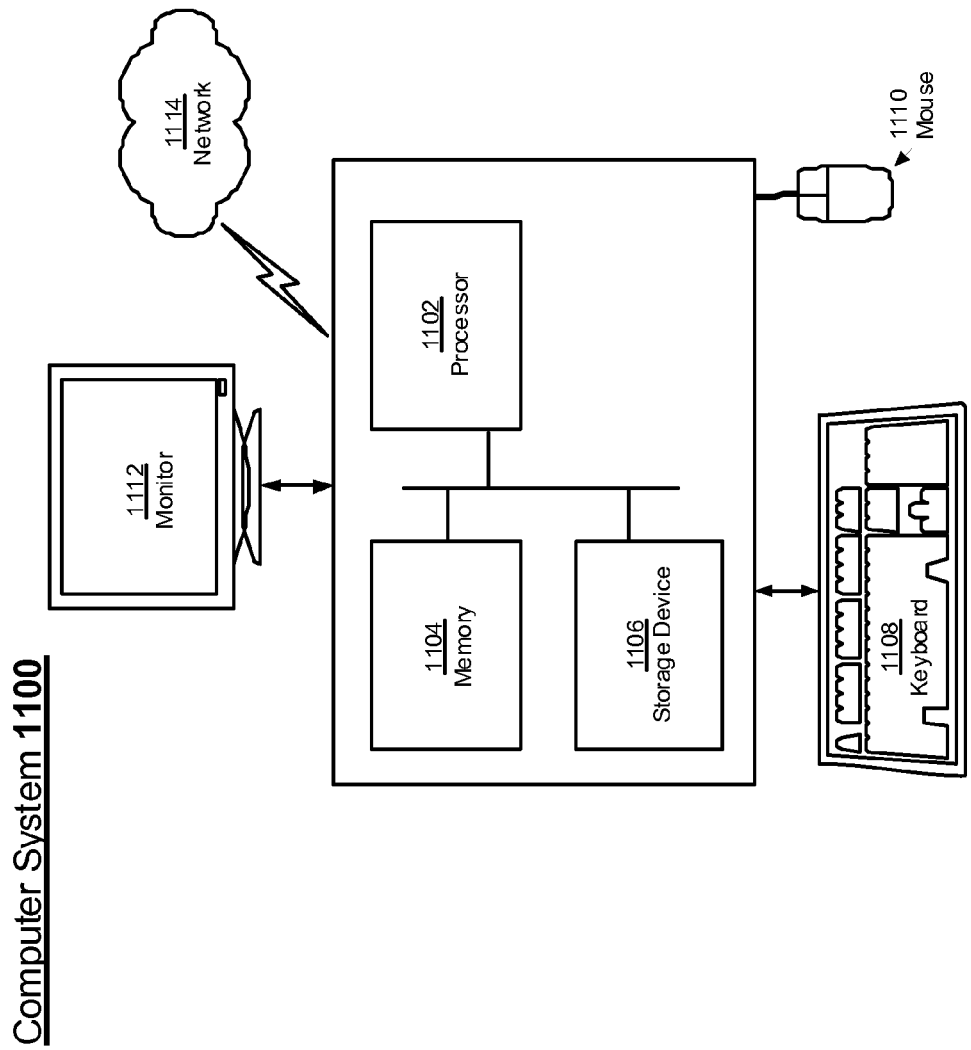
FIG. 11 shows a computer system in accordance with one or more embodiments of the invention.

Embodiments of the invention may be implemented on virtually any type of computer regardless of the platform being used. For example, as shown in FIG. 11, a computer system (1100) includes one or more processor(s) (1102), associated memory (1104) (e.g., random access memory (RAM), cache memory, flash memory, etc.), a storage device (1106) (e.g., a hard disk, an optical drive such as a compact disk drive or digital video disk (DVD) drive, a flash memory stick, magnetooptical discs, solid state drives, etc.), and numerous other elements and functionalities typical of today's computers or any future computer (not shown). Each processor may be a central processing unit and may or may not be a multi-core processor. The computer (1100) may also include input means, such as a keyboard (1108), a mouse (1110), a tablet (not shown), touch screen (not shown), a microphone (not shown), a digital camera (not shown), a microscope (not shown), etc. Further, the computer (1100) may include output means, such as a monitor (1112) (e.g., a liquid crystal display (LCD), a plasma display, or cathode ray tube (CRT) monitor). The computer system (1000) may be connected to a network (1114) (e.g., a local area network (LAN), a wide area network (WAN) such as the Internet, or any other type of network) via a network interface connection, wired or wireless (not shown). Those skilled in the art will appreciate that many different types of computer systems exist, and the aforementioned input and output means may take other forms including handheld devices such as tablets, smartphone, slates, pads, PDAs, and others. Generally speaking, the computer system (1100) includes at least the minimal processing, input, and/or output means necessary to practice embodiments of the invention.

Further, those skilled in the art will appreciate that one or more elements of the aforementioned computer system (1100) may be located at a remote location and connected to the other elements over a network. Further, embodiments of the invention may be implemented on a distributed system having a plurality of nodes, where each portion of the invention may be located on a different node within the distributed system. In one embodiment of the invention, the node corresponds to a computer system. Alternatively, the node may correspond to a processor with associated physical memory. The node may alternatively correspond to a processor or micro-core of a processor with shared memory and/or resources. Further, computer readable program code (e.g., software instructions) to perform embodiments of the invention may be stored on a computer readable medium. The computer readable medium may be a tangible computer readable medium, such as a compact disc (CD), a diskette, a tape, a flash memory device, random access memory (RAM), read only memory (ROM), or any other tangible medium.

While the invention has been described with respect to a limited number of embodiments, those skilled in the art, having benefit of this disclosure, will appreciate that other embodiments can be devised which do not depart from the scope of the invention as disclosed herein. Accordingly, the scope of the invention should be limited only by the attached claims.

What is claimed is:

1. A method for analyzing a tissue specimen comprising:
   obtaining a first digital tissue sample image showing a first tissue sample, wherein the first tissue sample is stained for a first biomarker, and wherein the first digital tissue sample image shows a first set of cells;

obtaining a second digital tissue sample image showing a second tissue sample, wherein the second tissue sample is stained for a second biomarker, wherein the second digital tissue sample image shows a second set of cells, and wherein the second set comprises a subset of the first set of cells;

analyzing the first digital tissue sample image to identify cells of the first tissue sample positive for the first biomarker;

analyzing the second digital tissue sample image to identify cells of the second tissue sample positive for the second biomarker;

identifying, on a per-cell basis, the subset of the first set of cells shown in the second digital tissue sample image;

performing, by a computer processor, and based on the identifying, co-expression analysis of the cells of the first tissue sample positive for the first biomarker and the cells of the second tissue sample positive for the second biomarker to create a biomarker co-expression profile, wherein the co-expression analysis identifies any cell in the subset positive for both the first biomarker and the second biomarker, any cell in the subset positive for only the first biomarker, and any cell in the subset positive for only the second biomarker; and displaying the biomarker co-expression profile.

2. A system for analyzing a tissue specimen comprising:
a processor;
a memory;
instructions stored in memory for causing the processor to:
obtain a first digital tissue sample image showing a first tissue sample, wherein the first tissue sample is stained for a first biomarker, and wherein the first digital tissue sample image shows a first set of cells;
obtain a second digital tissue sample image showing a second tissue sample, wherein the second tissue sample is stained for a second biomarker, wherein the second digital tissue sample image shows a second set of cells, and wherein the second set comprises a subset of the first set of cells;
analyze the first digital tissue sample image to identify cells of the first tissue sample positive for the first biomarker;
analyze the second digital tissue sample image to identify cells of the second tissue sample positive for the second biomarker;
identify, on a per-cell basis, the subset of the first set of cells shown in the second digital tissue sample image;
perform, based on the identifying, co-expression analysis of the cells of the first tissue sample positive for the first biomarker and the cells of the second tissue sample positive for the second biomarker to create a biomarker co-expression profile, wherein the co-expression analysis identifies any cell in the subset positive for both the first biomarker and the second biomarker, any cell in the subset a positive for only the first biomarker, and any cell in the subset positive for only the second biomarker; and
display the biomarker co-expression profile.

3. The system of claim 2, wherein the instructions further cause the processor to:
obtain a first biomarker control image showing a first biomarker control sample stained for the first biomarker, and wherein the first biomarker control sample has a pre-defined expression level for the first biomarker;
create a linear map of the pre-defined expression level for the first biomarker; and
select a cutoff point in the linear map, wherein the cutoff point distinguishes hues that represent positive portions from hues that represent negative portions in the first tissue sample, wherein analyzing the first digital tissue sample image comprises comparing each cell of the subset shown in first digital tissue sample image with the linear map.

4. The system of claim 2, wherein the instructions further cause the processor to:
obtain a first biomarker control image showing a first biomarker control sample stained for the first biomarker, and wherein the first biomarker control sample has a pre-defined expression level for the first biomarker;
defining a continuous scale of expression levels for the first biomarker based on the pre-defined expression level for the first biomarker; and
analyzing the first digital tissue sample image in relation to the continuous scale to identify an expression level of the first biomarker in the first tissue sample.

5. The system of claim 2, wherein the co-expression analysis comprises aligning the first digital tissue sample image with the second digital tissue sample image to identify the subset.

6. The system of claim 2, wherein the instructions further cause the processor to:
obtain a third digital tissue sample image of the first tissue sample; and
fuse the first digital tissue sample image with the third digital tissue sample image to obtain a single image of the first tissue sample.

7. The system of claim 2, wherein the instructions further cause the processor to:
perform light correction on the first digital tissue sample image using a third digital tissue sample image, wherein the third digital tissue sample image is an image of a portion of a slide void of the first tissue sample, wherein the first tissue sample is located on the slide.

8. The system of claim 2, wherein analyzing the first digital tissue sample image comprises identifying a location of each cell in the first digital tissue sample image, wherein analyzing the second digital tissue sample image comprises identifying a location of each cell in the second digital tissue sample image, and wherein identifying the subset comprises using the location of each cell in the first digital tissue sample image and the location of corresponding sections of the same cells in the second digital tissue sample image.

9. A non-transitory computer readable medium comprising computer readable program code stored thereon for causing a processor to:
obtain a first digital tissue sample image showing a first tissue sample, wherein the first tissue sample is stained for a first biomarker, and wherein the first digital tissue sample image shows a first set of cells;
obtain a second digital tissue sample image showing a second tissue sample, wherein the second tissue sample is stained for a second biomarker, wherein the second digital tissue sample image shows a second set of cells, and wherein the second set comprises a subset of the first set of cells;
analyze the first digital tissue sample image to identify cells of the first tissue sample positive for the first biomarker;
analyze the second digital tissue sample image to identify cells of the second tissue sample positive for the second biomarker;

identify, on a per-cell basis, the subset of the first set of cells shown in the second digital tissue sample image;

perform, based on the identifying, co-expression analysis of the cells of the first tissue sample positive for the first biomarker and the cells of the second tissue sample positive for the second biomarker to create a biomarker co-expression profile, wherein the co-expression analysis identifies any cell in the subset positive for both the first biomarker and the second biomarker, any cell in the subset positive for only the first biomarker, and any cell in the subset positive for only the second biomarker; and display the biomarker co-expression profile.

10. The non-transitory computer readable medium of claim 9, wherein the computer readable program code further cause the processor to:

obtain a first biomarker control image showing a first biomarker control sample stained for the first biomarker, and wherein the first biomarker control sample has a pre-defined expression level for the first biomarker;

create a linear map of the pre-defined expression level for the first biomarker; and select a cutoff point in the linear map, wherein the cutoff point distinguishes hues that represent positive portions from hues that represent negative portions in the first tissue sample, wherein analyzing the first digital tissue sample image comprises comparing each cell of the subset shown in the first digital tissue sample image with the linear map.

11. The non-transitory computer readable medium of claim 9, wherein the computer readable program code further cause the processor to:

obtain a first biomarker control image showing a first biomarker control sample stained for the first biomarker, and wherein the first biomarker control sample has a pre-defined expression level for the first biomarker;

defining a continuous scale of expression levels for the first biomarker based on the pre-defined expression level for the first biomarker; and analyzing the first digital tissue sample image in relation to the continuous scale to identify an expression level of the first biomarker in the first tissue sample.

12. The non-transitory computer readable medium of claim 9, wherein the co-expression analysis comprises aligning the first digital tissue sample image with the second digital tissue sample image to identify the subset.

13. The non-transitory computer readable medium of claim 9, wherein the computer readable program code further cause the processor to:

obtain a third digital tissue sample image of the first tissue sample; and fuse the first digital tissue sample image with the third digital tissue sample image to obtain a single image of the first tissue sample.

14. The non-transitory computer readable medium of claim 9, wherein the computer readable program code further cause the processor to:

perform light correction on the first digital tissue sample image using a third digital tissue sample image, wherein the third digital tissue sample image is an image of a portion of a slide void of the first tissue sample, wherein the first tissue sample is located on the slide.

15. The non-transitory computer readable medium of claim 9, wherein performing the co-expression analysis comprises:

aligning the first digital tissue sample image with the second digital tissue sample image.

16. The non-transitory computer readable medium of claim 9, wherein analyzing the first digital tissue sample image comprises identifying a location of each cell in the first digital tissue sample image, wherein analyzing the second digital tissue sample image comprises identifying a location of each cell in the second digital tissue sample image, and wherein identifying the subset comprises using the location of each cell in the first digital tissue sample image and the location of each cell in the second digital tissue sample image, and wherein the information is used to identify cells positive for the first biomarker and the second biomarker, positive for only the first biomarker, and positive for only the second biomarker.

17. The non-transitory computer readable medium of claim 16, wherein performing the co-expression analysis disregards cells not present in the first digital tissue sample image and the second digital tissue sample image.

18. The non-transitory computer readable medium of claim 9, wherein the biomarker co-expression profile is displayed in a tabular form.

19. The non-transitory computer readable medium of claim 9, wherein the biomarker co-expression profile is displayed as a graphical image.

20. The non-transitory computer readable medium of claim 19, wherein each cell in the graphical image is displayed with an artificial color indicating whether the cell is positive for one selected from a group consisting of both the first biomarker and the second biomarker, positive for only the first biomarker, positive for only the second biomarker, and negative for both the first biomarker and the second biomarker.

21. The non-transitory computer readable medium of claim 9, wherein the biomarker co-expression profile is used to determine the efficacy of drug treatment plan for a disease.

\* \* \* \* \*